United States Patent [19]

Ismail

[11] Patent Number: 5,422,283
[45] Date of Patent: Jun. 6, 1995

[54] SOLID-PHASE INTERFEROMETRIC IMMUNOASSAY SYSTEM

[75] Inventor: Ashraf Ismail, Westmount, Canada

[73] Assignee: The Royal Institution for the Advancement of Learning, Montreal, Canada

[21] Appl. No.: 185,170

[22] Filed: Jan. 24, 1994

Related U.S. Application Data

[63] Continuation of Ser. No. 931,417, Aug. 24, 1992, abandoned, which is a continuation of Ser. No. 482,870, Feb. 22, 1990, abandoned.

[51] Int. Cl.⁶ .................. G01N 33/53; G01N 33/552; G01N 33/546; G01B 9/02
[52] U.S. Cl. ........................ 436/525; 436/527; 436/533; 435/973; 435/7.1; 435/808; 435/287; 356/346
[58] Field of Search ............. 435/7.1, 287, 288, 808; 435/973; 422/82.04, 82.05, 82.06, 82.07, 82.08, 82.09, 82.11; 436/518, 525, 527, 531, 533, 534; 356/356, 343, 363, 346

[56] References Cited

U.S. PATENT DOCUMENTS

| | | | |
|---|---|---|---|
| 4,305,925 | 10/1981 | Kapmeyer et al. | 422/56 |
| 4,552,723 | 11/1985 | Adams et al. | 422/70 |
| 4,775,637 | 10/1988 | Sutherland et al. | 436/527 |
| 4,780,423 | 10/1988 | Bluestein et al. | 436/527 |
| 4,818,710 | 4/1989 | Sutherland et al. | 436/527 |
| 4,837,168 | 7/1989 | de Jaeger et al. | 436/533 |
| 4,843,243 | 7/1989 | Biemann et al. | 422/70 |
| 4,877,747 | 10/1989 | Stewart | 436/525 |
| 4,880,752 | 11/1989 | Keck et al. | 435/288 |
| 4,992,385 | 2/1991 | Godfrey | 436/525 |
| 5,120,131 | 6/1992 | Lukosz | 356/351 |
| 5,149,626 | 9/1992 | Fleming | 435/7.1 |
| 5,171,695 | 12/1992 | Ekins | 436/808 |
| 5,268,305 | 12/1993 | Ribi et al. | 422/82.05 |

FOREIGN PATENT DOCUMENTS

| | | |
|---|---|---|
| 0073980 | 3/1983 | European Pat. Off. |
| 167335 | 1/1986 | European Pat. Off. |
| 0171148 | 2/1986 | European Pat. Off. |
| 254575 | 1/1988 | European Pat. Off. |
| 2125547 | 3/1984 | United Kingdom ............ 435/973 |
| 8402578 | 7/1984 | WIPO |
| 8601901 | 3/1986 | WIPO |
| WO88/00696 | 1/1988 | WIPO |
| WO88/07202 | 9/1988 | WIPO |
| WO89/07756 | 8/1989 | WIPO |

OTHER PUBLICATIONS

Webster's Dictionary, pp. 628, 825, 1984, MA.
Webster 9th New Collegiate Dictionary p. 631.

*Primary Examiner*—Robert J. Warden
*Assistant Examiner*—Theresa T. Snider
*Attorney, Agent, or Firm*—Cushman, Darby & Cushman

[57] ABSTRACT

The present invention relates to a solid-phase immunoassay system for the determination of an antibody or an antigen in a sample which consists of an interferometric signal from an optical source, a solid support coated with an antibody or an antigen and having at least one region immersed in a solution containing a sample, thereby the corresponding antigen or antibody can be complexed on the solid support, an optical transfer and focusing system to measure the interferometric signal after its transmission (or reflectance) by the solid support, and a measuring device to record and process the interferometric signal at a wavelength corresponding to an absorption characteristic of the antigen-antibody complex or of a label incorporated into the antigen-antibody complex, thereby determining the amount of antigen or antibody in the sample.

10 Claims, 5 Drawing Sheets

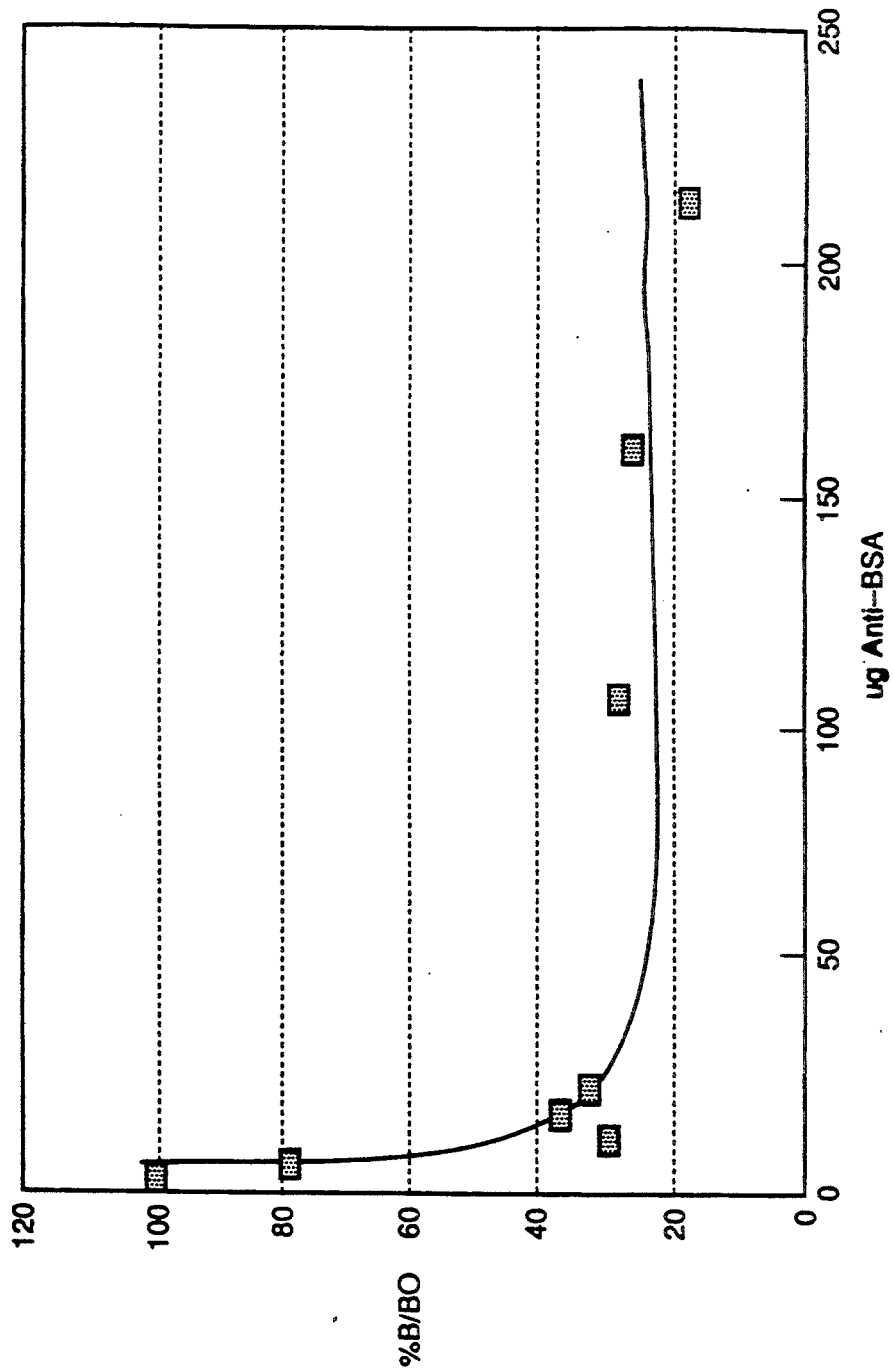

SOLID-PHASE INTERFEROMETRIC IMMUNOASSAY SYSTEM

This is a continuation of application Ser. No. 07/931,417, filed on Aug. 24, 1992, which was a continuation of application Ser. No. 07/482,870, filed on Feb. 22, 1990, which was abandoned upon the filing hereof.

BACKGROUND OF THE INVENTION

With the advent of radioimmunoassay (RIA) (Yalow and Berson, (1960), *J. Clin. Invest.*, 39:1157), the immunoassay became recognized as an exquisitely sensitive tool in the measurement of clinically important substances found at low concentrations in various body fluids.

U.S. Pat. No. 3,654,090 which issued to Schuurs on Apr. 4, 1972, teaches the use of an enzyme-substrate system to replace the radioactive label used in the RIA.

Both of these assays make use of a competitive reaction between a limited number of antibody molecules and both a labeled antigen and unlabeled antigen (either known amounts used to construct a standard curve or unknown amounts contained in test samples). The more unlabeled antigen in the reaction mixture, the less labeled antigen will be bound to the limited number of antibody molecules. One must be equipped with a method to detect the ratio of bound to free labeled antigen.

The earliest methods used a physical separation of antibody-bound labeled antigen from free labeled antigen. This type of assay in which a separation step is employed is referred to as a heterogeneous assay.

The assays referred to above all make use of antigen or hapten (a low molecular weight substance which is not immunogenic but is capable of being bound by specific anti-hapten antibodies) which is identical or immunochemically analogous to the analyte (the unknown being tested for). The antigen or hapten is labeled with reagent means for determining the extent to which the labeled antigen or hapten is bound to the antibody. The use of such substances presents problems in the various assay systems already developed in the art.

For example, various drawbacks are associated with the use of radioisotopes, such as high cost, limited shelf-life, radiolysis of the sample, and licensing and disposal restrictions. The drawbacks associated with the use of enzymes as labels include: sensitivity to temperature and buffer variation, limited shelf-life in solution, and susceptibility to degradation by lytic enzymes that may be present in the sample to be analyzed.

FTIR spectrometers have been found to be very useful in the analysis of weak signals from opaque samples. Surface analysis can also be carried out routinely by reflectance techniques. Detection limits in the nanogram to picogram range have been cited in the literature for FTIR spectrometers.

It would be highly desirable if there could be a solid-phase immunoassay system using FTIR techniques. That is, an interferometrically coded signal from a mid-infrared source transmitted through, or reflected from, a solid support surface where the resulting attenuation of the signal by a label attached to an antibody or antigen would provide a measurement of an antigen-antibody complex on the solid support surface. Such a system would provide a heterogeneous immunoassay method that would offer several advantages with respect to existing heterogeneous immunoassay methods. Such a system would be unaffected by background fluorescence or phosphorescence, unlike existing heterogeneous immunoassay systems that employ fluorescent tags.

SUMMARY OF THE INVENTION

Surprisingly and in accordance with the present invention, there is provided a solid support heterogeneous immunoassay (SPIRIT) for the determination of the presence of an
- a mid-infrared source;
- an interforometer to convert the source radiation into an interferometric signal;
- an interferometric signal from an optical source;
- a solid support coated with an antibody, an antibody binder protein or an antigen and having at least one region immersed in a solution containing a sample, whereby the corresponding antigen or antibody can be complexed on said solid support;
- an optical transfer and focusing system to measure the interferometric signal after its transmission through the solid support; and
- a measuring device to record and process the interferometric signal for determining the degree of attenuation of the interferometric signal at a wavelength corresponding to an absorption characteristic of a label incorporated into the antigen-antibody complex, thereby the amount of antigen or antibody in the sample is determined.

Such a heterogeneous immunoassay system can be utilized for the determination of any antigen or antibody.

Such a heterogeneous immunoassay system can be utilized for the simultaneous determination of multiple analytes in a single heterogeneous immunoassay test.

Although the present invention has been described in the foregoing description by way of preferred embodiments thereof, it should be pointed out that it can be modified at will, within the nature of the present invention.

for their respective antibody binding sites ($ab_1$, $ab_2$, $ab_3$); and

FIG. 7 shows a curve representing a competition between antibodies bound to a solid support and a known amount of labeled antigen (ag*) in the surrounding solution competing for the antibody binding sites with free antigen (ag);

DETAILED DESCRIPTION OF THE INVENTION

Figure 1:
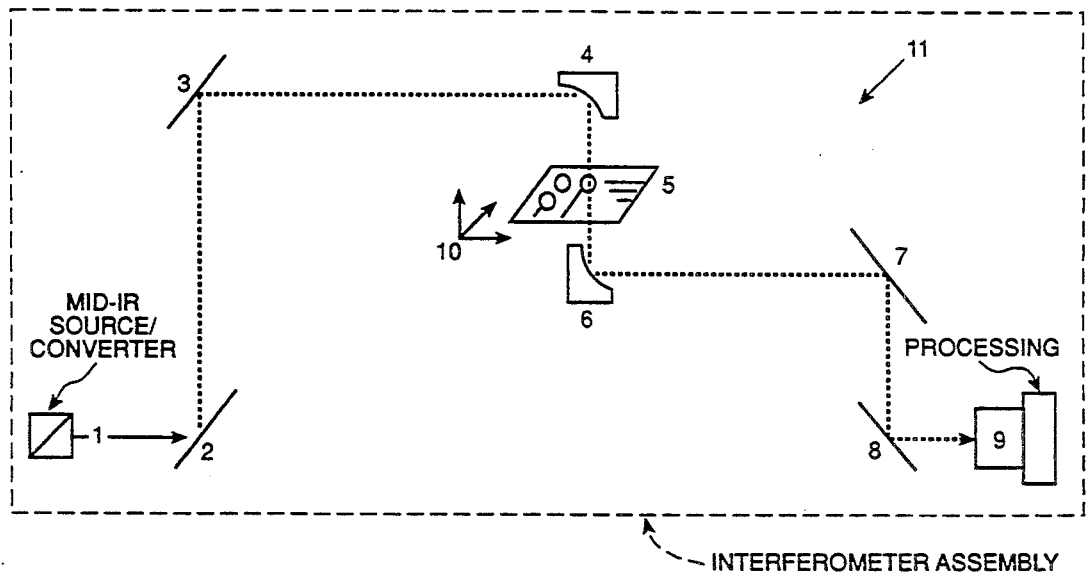
FIG. 1 shows a schematic representation of one embodiment of the heterogeneous immunoassay system made in accordance with the present invention.

An embodiment of the heterogeneous immunoassay system according to the present invention is shown in FIG. 1 and is generally denoted 11. It mainly consists in a focusing and optical transfer system of the interferometric signal 1, in which there are: flat mirrors 2, 3, 7, 8, beam focusing mirrors 4, 6, a translation stage 10, and a detector element 9.

The device adapted to measure the interferometric signal mainly consists in the flat mirrors 2, 3, 7, 8 and the beam focusing mirrors 4, 6.

Figure 2:
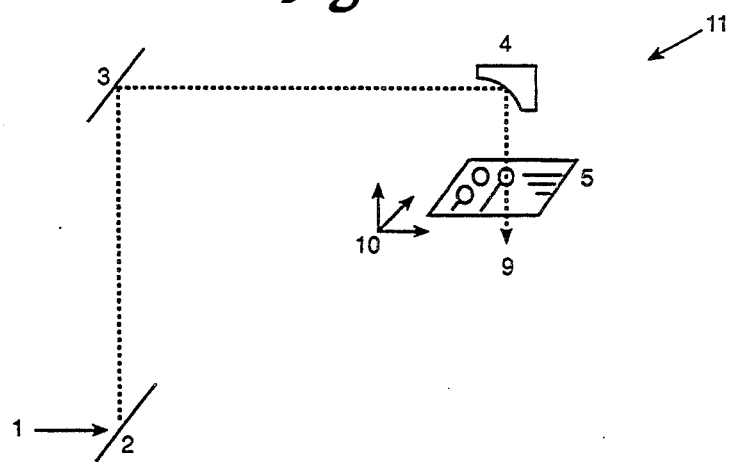
FIG. 2 shows a schematic representation of another embodiment of the heterogeneous immunoassay system made in accordance with the present invention.

The use of a beam condenser 4 to focus the interferometric signal onto the solid support 5 aids in increasing the throughput of the signal reaching the detector 9. A detector element 9 can be placed directly below the translation stage 10 to enhance signal detection from the solid support (FIG. 2).

The use of multiple detectors 9 and split interferometric signal or multiple light sources instead of a beam focusing mirror 4 can decrease sample analysis time. This technique is used for noninterferometric systems.

The heterogeneous immunoassay system of the present invention is an immunoassay where one or several separation steps are required. In this assay, a solid support coated with an antigen (or antibody) is brought in contact with a solution containing the corresponding antibody (or antigen). Subsequent to incubation, the bound fraction, consisting of the antigen-antibody complex on the solid support, is obtained by aspiration or filtration of the solution and washing and drying of the solid support. The interferometrically coded signal is transmitted through the solid support. The measured absorbance is proportional to the amount of antigen-antibody complex present per surface area:

$$A \alpha n/r^2$$

where n is the number of moles of antigen-antibody complex, and r is the diameter of the solid support, r being equal to or less than the diameter of the focused signal emanating from the beam condenser.

Any solid support having little or no absorption in the wavelength region where a characteristic absorption of the antigen-antibody complex occurs can be employed in a heterogeneous solid support immunoassay system.

As solid support there may be used a polymer membrane, a polymer slide, a polymer film, a polymer solution, or a polymer suspension. A solid support n-ray also be a reflecting metal surface, a metal mesh or a metal grid, a filter, a salt crystal, a disk, or a pellet or a glass slide or tube.

Functional groups that can covalently bind the antibody or antigen can be introduced onto a solid support by a variety of methods. In accordance with the present invention, carboxy-activated or amino-modified polymer membranes (or films) or carboxy-modified (or amino-modified) or unmodified latex particles are employed as preferred solid supports in the heterogeneous solid-phase interferometric immunoassay system.

Also, a solid support (e.g., $CaF_2$ or glass slide) can be coated with a functionalized polymer film by immersion methods, the thickness of the film being controlled by the concentration of the polymer in the solution in which the solid support is immersed. The polymer employed is a carboxy-modified latex polymer. The thickness of the coating is estimated from the intensities of the infrared peaks due to absorptions of the polymer film. The antigen or antibody can be adsorbed on the polymer support or it can be covalently linked to the polymer through the carboxyl function. Other methods of thin film deposition can also be utilized to coat the solid support with an antigen, antibody or antibody binder.

The underlying principle of immunoassay is that the concentration of the antigen-antibody complex is proportional to the concentration of free antigen and free antibody present in the assay medium. Thus, a calibration curve for the determination of an antigen (or antibody) can be constructed by measuring the amount of antigen-antibody complex formed upon addition of varying and known amounts of antigen (or antibody) to a solution containing a fixed and known amount of antibody (or antigen). In terms of the present invention, the antigen-antibody complex is formed on a solid support (FIG. 5), the solid support is rinsed to remove any free antigen (or antibody), then dried, and the amount can be determined by measuring the attenuation of the interferometric signal subsequent to incubation and washing steps. The attenuation of the interferometric signal is measured at a wavelength corresponding to a characteristic absorption of a specifically introduced label that can be readily detected. Organometallic molecules or latex particles having characteristic absorptions in the mid-infrared frequency range have been employed thus far as labels in the demonstration of the general viability of a heterogeneous interferometric immunoassay.

Several different types of solid support heterogeneous interferometric immunoassay measurement protocols are possible using the heterogeneous immunoassay system of the present invention. By referring to the numerals previously defined and shown in FIGS. 1 to 4, the following measurement protocols may be constructed:

A) 1→2→3→4→5→6→7→8→9 (FIG. 1);
B) 1→2→3→4→5→9 (FIG. 2);
C) 1→2→3→4→5*→9 (FIG. 3); and
D) 1→2→3→4→5→7→8→9 (FIG. 4).

In FIG. 1, the heterogeneous immunoassay system made in accordance with the present invention mainly consists in a focusing and optical transfer of the interferometric signal 1, in which there are: flat mirrors 2,3,7,8, beam focusing mirrors 4,6, a sample 5, a translational stage 10, and a detector 9. The two beam focusing mirrors 4,6 serve as an optical focusing of the interferometric signal to the sample on the solid support 5 and then to the detector element 9.

In FIG. 2, the heterogeneous immunoassay system made in accordance with the present invention mainly consists in a focusing and optical transfer of the interferometric signal 1, in which there are: flat mirrors 2,3, beam focusing mirror 4, a translational stage 10, and a detector 9 placed below the sample 5. The beam focusing mirror 4 serves as an optical focusing of the interferometric signal to the sample on the solid support 5 and the interferometric signal is transmitted through the solid support to the detector 9.

Figure 3:
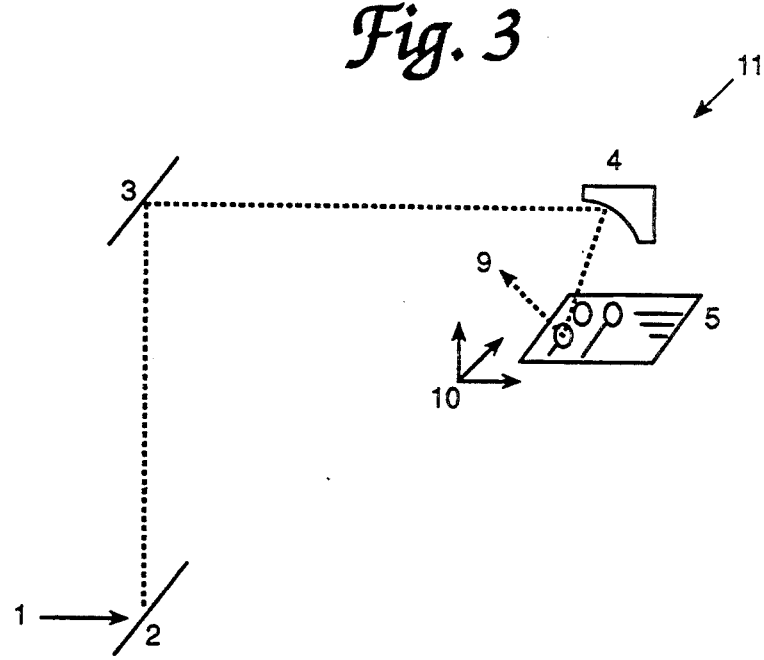
FIG. 3 shows a schematic representation of another embodiment of the heterogeneous immunoassay system made in accordance with the present invention.
Figure 4:
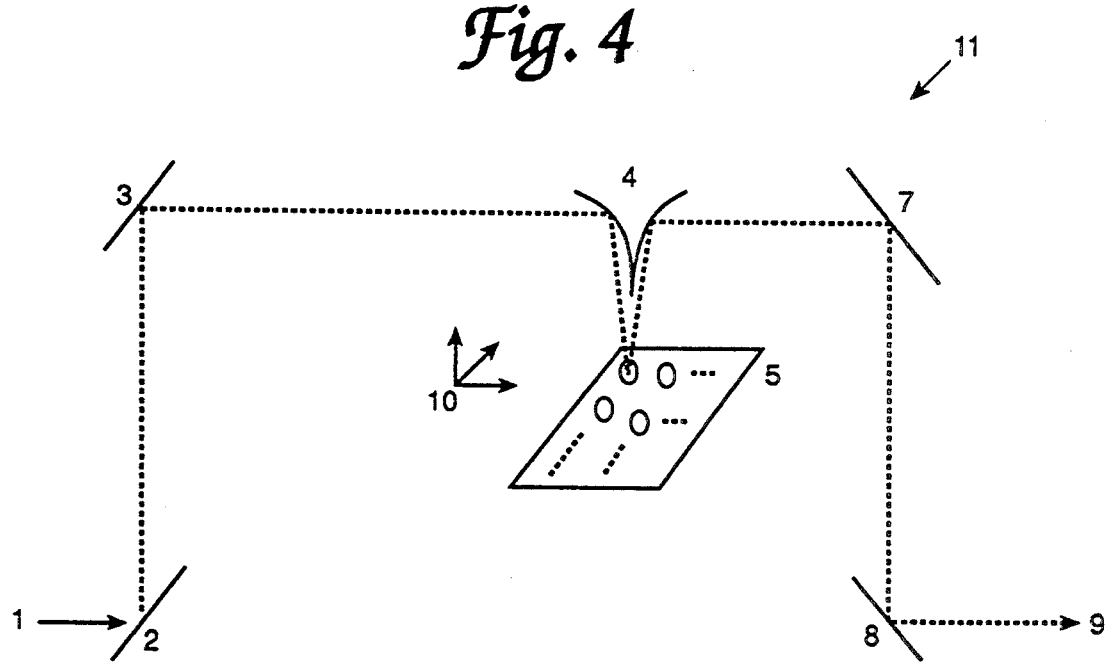
FIG. 4 shows a schematic representation of another embodiment of the heterogeneous immunoassay system made in accordance with the present invention.

In FIG. 3, the heterogeneous immunoassay system made in accordance with the present invention mainly consists in a focusing and optical transfer of the interferometric signal 1, in which there are: flat mirrors 2,3, beam focusing mirror 4, a sample 5* on a reflecting surface, a translational stage 10, and a detector 9 placed above the sample. The beam focusing mirror 4 serves as an optical focusing of the interferometric signal to the sample on a reflecting surface such as a metallic solid support 5* and the interferometric signal is reflected off the metallic solid support and onto a detector element above the solid support 5*.

In FIG. 4, the heterogeneous immunoassay system made in accordance with the present invention mainly consists in a focusing and optical transfer of the interferometric signal 1, in which there are: flat mirrors 2,3, two concave mirrors adjacent to one another 4, which serve to transfer the interferometric signal to the sample 5, and its reflectance from the sample 5, with flat mirrors 7;8 to the detector 9 and a translational stage 10. The two concave mirrors adjacent to one another serve to transfer the interferometric signal to the sample on the solid support and its reflectance from the solid support to the detector 9.

Figure 5:
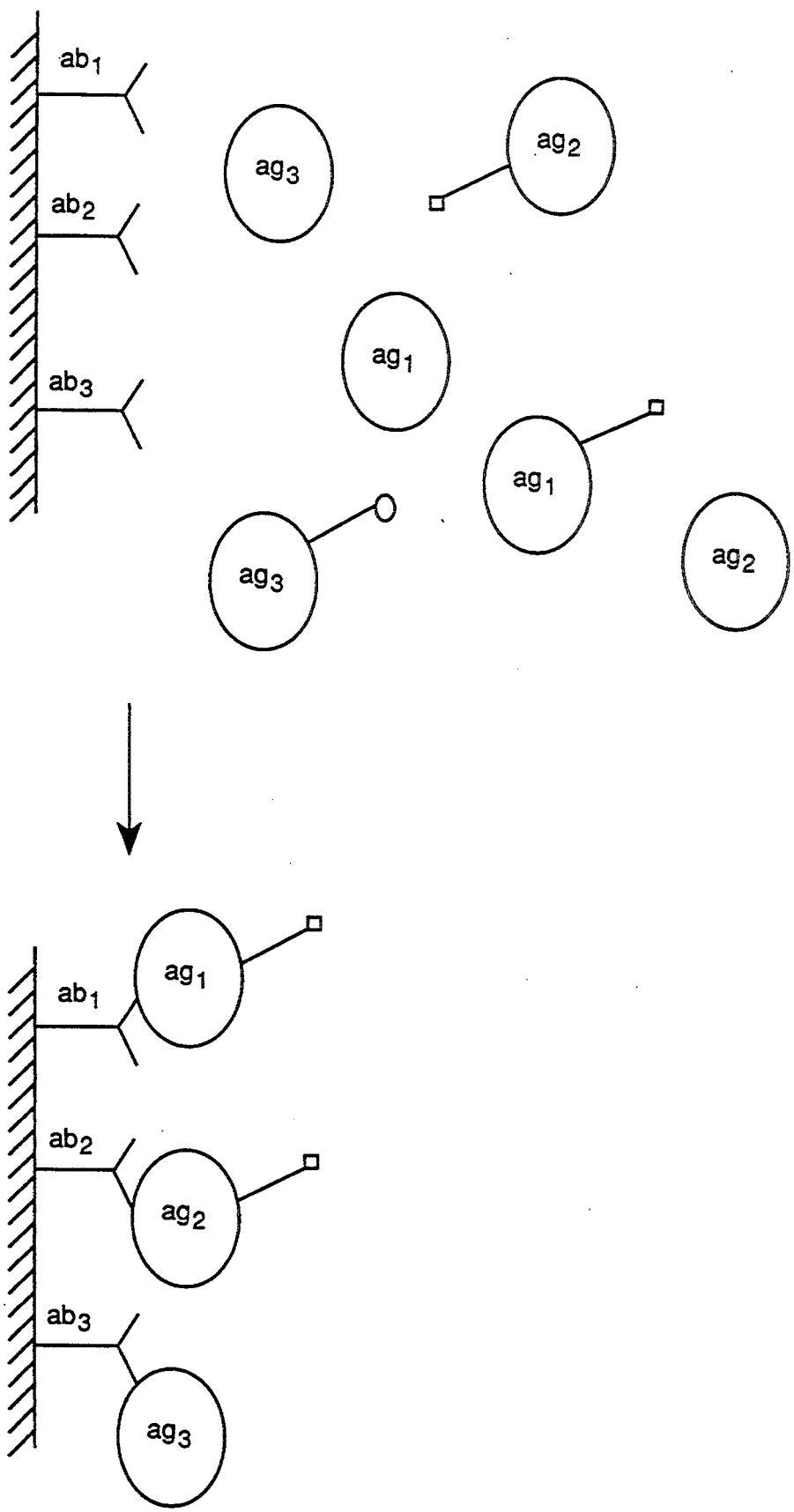
FIG. 5 shows a heterogeneous immunoassay system for detecting multiple antigens ($ag_1$, $ag_2$, $ag_3$) according to the present invention in which antibodies ($ab_1$, $ab_2$, $ab_3$) are bound to the solid support, and a known amount of labeled antigens ($ag_1^*$, $ag_2^\#$, $ag_3^@$), each of the labeled antigens having distinct and characteristic absorptions, in the surrounding solution compete for the antibody binding sites with unlabeled antigens.

A solid support heterogeneous immunoassay system for the detection of antigens ($ag_1$, $ag_2$, $ag_3$) has the antibodies ($ab_1$, $ab_2$, $ab_3$) bound onto the solid support, and a known amount of labeled antigens ($ag_1^*$, $ag_2^\#$, $ag_3^@$) in the surrounding solution competes for the antibody binding sites with the unlabeled antigen (FIG. 5).

Figure 6:
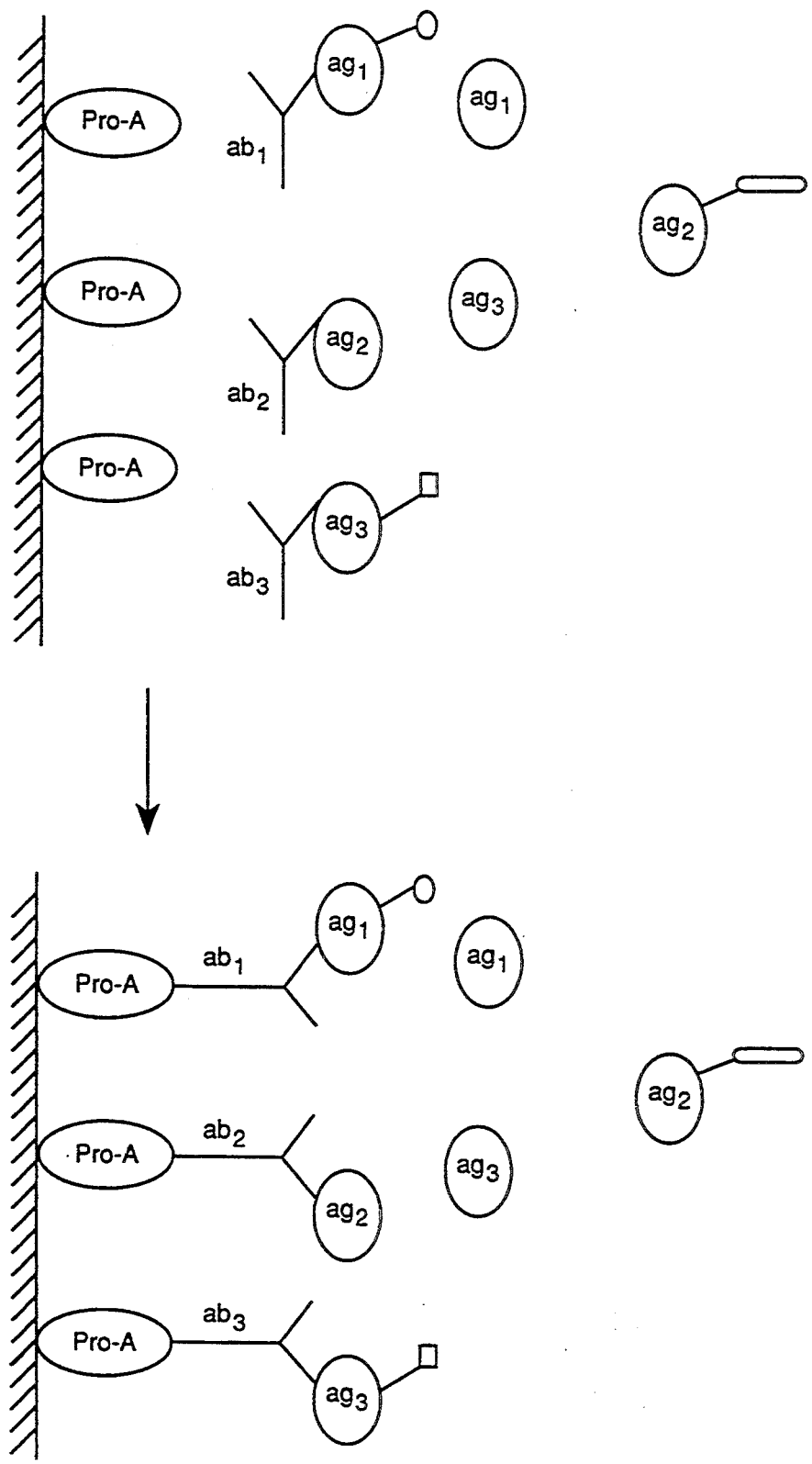
FIG. 6 shows a heterogeneous immunoassay system where an antibody binder is bound to the solid support according to the present invention and the surrounding solution consists of labeled antigens ($ag_1^*$, $ag_2^\#$, $ag_3^@$) competing with the unlabeled antigens ($ag_1$, $ag_2$, $ag_3$)

A solid support heterogeneous immunoassay system for the detection of an antigen (ag) has the antibody (ab), antigen (ag) and labeled antigen (ag*) in the surrounding solution and an antibody binder (ab-B) bound onto the solid support (FIG. 6).

A solid-phase heterogeneous immunoassay system for the detection of an antigen (ag) has the antibody binder protein bound onto the solid support latex particles, and a known amount of labeled antigen (ag*) in the surrounding solution compete for the antibody binding, sites with the unlabeled antigen.

The present invention will be more readily understood by referring to the following examples which are given to illustrate the invention rather than to limit its scope.

EXAMPLE I

Heterogeneous solid-phase interferometric immunoassay with the use of a labeled antigen The solid-phase immunoassays were carried out utilizing Immunodyne ® I and II membranes (Pall Corporation). Immunodyne ® membranes consist in part of a partially hydrolyzed nylon where the carboxy groups are activated in order to covalently bind antibodies. The two types of Immunodyne ® membranes differ in the nature of activating group complexed to the carboxyl function. In the following experiments, Immunodyne ® I (Lot #0.45HMA80705A-2) and Immunodyne ® II (Lot #0.45HLP71124A) were employed. The membranes were stored in a vacuum desiccator prior to use in antibody immobilization.

The analyses were performed on a Bomem Michelson ® 100 FT-IR spectrometer (operating at 4 cm$^{-1}$ resolution) equipped with a liquid-nitrogen cooled InSb or a DTGS detector. A beam condenser (4×) was utilized to focus the beam from the optical source onto the membrane in the sample compartment. Spectral acquisition and processing were handled by the software supplied with the instrument.

Immobilization of antibody on the solid support

Anti-BSA (13.4 mg) was dissolved in 1 ml of phosphatebuffered saline, pH 7.2 (PBS), and the solution was pipeted onto the membrane (Immunodyne ® I) over an area of 6 cm$^2$. The membrane was then allowed to dry overnight in air at room temperature.

Construction of the titration curve for anti-BSA

Bovine serum albumin (BSA) was labeled with a metal tricarbonyl moiety by the procedure described in U.S. patent application Ser. No. 409, 788, filed on Sep. 20, 1989, now abandoned, and the disclosure of which is herein incorporated by reference. The labeled BSA is henceforth denoted as BSA-X(CO)$_3$.

Stock solution I was prepared by dissolving 131.2 mg of BSA in 2 ml of PBS. Stock solution II was prepared by dissolving 38.5 mg of BSA-X(CO)$_3$ in 800 ul of PBS. Six solutions were made in 10-ml beakers using the volumes of the above solutions shown in Table I.

TABLE I

| Beaker | Soln. I | Soln. II | Buffer |
| --- | --- | --- | --- |
| 1 | 0 | 100 ul | 900 ul |
| 2 | 50 ul | 100 ul | 850 ul |
| 3 | 100 ul | 100 ul | 800 ul |
| 4 | 200 ul | 100 ul | 700 ul |
| 5 | 600 ul | 100 ul | 300 ul |
| 6 | 900 ul | 100 ul | 0 |

The solutions were mixed thoroughly. The membrane was cut into six pieces of 1 cm$^2$ surface area, and one piece was placed into each of the beakers. The beakers were covered with aluminum foil and left in a refrigerator at 4° C. overnight. After this period, the membranes were washed first with the buffer solution and then with distilled water. This was accomplished by shaking the membrane in the liquid for about 20 s. They were then left to dry in presence of air for about 1 h. Each sample was then analyzed by measuring the attenuation of the interferometric signal at a wavelength corresponding to a v(CO) absorption of the label. The titration curve was constructed by plotting the attenuation measured for each membrane sample as a function of the amount of BSA present in the solution in which the membrane was immersed.

Construction of the standard curve for anti-BSA

From the titration curve, the most appropriate concentration of the BSA-X(CO)$_3$ for the generation of a standard competition curve was estimated at 60 ug/500 ul. An anti-BSA solution was prepared by dissolving 5 mg of anti-BSA in 2 ml of PBS to yield a final concentration of 2.5 mg/ml. Into each of nine test tubes, a 5-mm-diameter circular disk of Immunodyne ® II with anti-BSA bound to the surface was placed. Solutions containing a fixed amount of BSA-X(CO)$_3$ and varying amounts of anti-BSA were added to the test tubes. The solutions were vortexed and left in the dark for 3 h at room temperature. The solution was decanted and the membranes were rinsed with PBS, and then briefly with water and dried for 20 min. Each sample was then analyzed by measuring the attenuation of the interferometric signal at a wavelength corresponding to a v(CO) absorption of the label. The attenuation measured for each membrane sample (B) with respect to that measured for the membrane incubated in the absence of anti-BSA (B$_0$) was plotted as a function of the amount of anti-BSA present in the solution in which the membrane was immersed to generate the standard curve (FIG. 7).

EXAMPLE II

Construction of a titration curve for monclonal antibodies to phosphoryl choline with the use of a labeled antibody binder Protein-A (pro-A, product of Sigma) was labeled with a metal tricarbonyl moiety by the procedure described in U.S. patent application Ser. No. 409, 788 filed on Sep. 20, 1989, now abandoned, and the disclosure of which is herein incorporated by reference. The labeled pro-A is henceforth denoted as pro-A-$X(CO)_3$.

BSA-PC conjugate (two PC molecules per BSA) was immobilized onto an Immunodyne ® II membrane following the procedure outlined in Example I. The membrane was sectioned into 5-mm disks. The disks were incubated with different dilutions of anti-PC in PBS for 2 h. Following decantation of the solutions, the membranes were washed three times with PBS. Each membrane was then incubated in a solution of pro-A-$X(CO)_3$ in PBS (1 mg/ml) for 1 h at room temperature. The solution was decanted and the membrane was washed twice with PBS solution and once with distilled water and dried. The interferometric signal was recorded through the membrane by placing the membrane against the detector window. The titration curve was constructed by plotting the attenuation at a wavelength corresponding to a $\nu(CO)$ absorption of the label measured for each membrane sample as a function of the amount of anti-PC present in the solution in which the membrane was immersed.

EXAMPLE II

Construction of a titration curve for the use of an antibody binder immobilized onto a solid support A 5-cm Immunodyne ® II membrane disk was immersed in 2.5 ml of a solution of pro-A in PBS (1 mg/ml) and shaken for 1 h at room temperature. Following decantation of the solution, the membrane was rinsed three times with PBS. The membrane was then incubated with 5 ml of a solution of casein in PBS (1–10% w/v) for 1 to 16 h at 4° C. to block the activated groups on the membrane surface that did not bind pro-A in the first step. Six solutions containing a fixed amount of BSA-$X(CO)_3$ and varying amounts of anti-BSA were prepared and left to stand for 1 h at room temperature. A 5-mm-diameter piece of the membrane coated with pro-A was dropped into each solution. After shaking for 1 h at room temperature, the solution was decanted and the membrane was washed twice with buffer, once with distilled water, and dried in air. Each sample was then analyzed by measuring the attenuation of the interferometric signal at a wavelength corresponding to a $\nu(CO)$ absorption of BSA-$X(CO)_3$. The titration curve was constructed by plotting the attenuation measured for each membrane sample as a function of the amount of anti-BSA present in the solution in which the membrane was immersed.

EXAMPLE IV

Demonstration of the viability of the use of latex particles in solid-phase interferometric immunoassay In this example, carboxy-modified latex (CML) particles (product of Seradyn Corp.) were used as the solid support in interferometric immunoassay. Pro-A was covalently bound to the carboxy groups present on the surface of the CML particles by the following procedure. To 2 ml of a solution of pro-A in PBS (1 mg/ml) was added 100 ml of a suspension of CML in $H_2O$ (30% w/v) and 10 mg of water-soluble carbodiimide (WSC). The mixture was stirred overnight at 4° C. and then dialyzed (molecular weight cutoff, 12,000) against PBS to remove the WSC and centrifuged five times, with the supernatant decanted each time and replaced with a fresh buffer solution. The CML-[pro-A]$_n$ particles were resuspended in 2 ml of PBS. In a separate test tube, BSA-$X(CO)_3$ (0.1 mg) was incubated with antiBSA (0.1 mg) in PBS (300 ul) for 1 h at room temperature. A 100-ul aliquot of the suspension of CML-[pro-A]$_n$ particles was added to this solution. This mixture was shaken for 1 h at room temperature and then filtered through a cellulose acetate membrane under vacuum. The particles were washed twice with PBS and once with distilled water and dried under vacuum. The sample was then analyzed by measuring the attenuation of the interferometric signal through the cellulose acetate membrane at a wavelength corresponding to a $\nu(CO)$ absorption of BSA-$X(CO)_3$. The attenuation of the interferometric signal was also recorded from the surface of the cellulose acetate membrane with the use of a DRIFT ® accessory (product of Spectratech). In both cases, the absorption of the $X(CO)_3$ label was detected, demonstrating the viability of the use of latex particles as a solid support in a heterogeneous interferometric immunoassay.

EXAMPLE V

Demonstration of the viability of the use of latex particles in solid-phase agglutination interferometric immunoassay In this example, latex particles (product of Seradyn Corp.) were used as the solid support and label in an agglutination interferometric immunoassay. BSA was adsorbed onto the surface of the latex particles by the following procedure. To 2 ml suspension of latex (L) particles (1% w/v) in PBS was added 40 mg of BSA. The mixture was shaken overnight at 4° C. and then centrifuged twice, with the supernatant decanted each time and replaced by a fresh buffet solution. The L-BSA particles were resuspended in 2 ml of PBS. In separate tubes, increasing amounts of anti-BSA (0–80 ul of 2 mg/ml anti-BSA in PBS) were added in a fixed incubation volume (100 ul), and 50 ul of L-BSA suspension was then added to each tube and left to stand overnight at 4° C. The latex particles were found to precipitate to a different extent in each tube. The supernatant was pipeted out and coevaporated with 25 ul of a saturated KBr solution. The resulting solid was pressed into a pellet and the sample was then analyzed by measuring the attenuation of the interferometric signal through the pellet at a wavelength characteristic of the latex particle. The titration curve was constructed by plotting the attenuation measured for each pellet as a function of anti-BSA present in the solution in which the latex particles were added. A second titration curve was constructed by depositing the precipitated (agglutinated) fraction on a copper grid (mesh 400) (J.B. #EM Services Inc.) and plotting the attenuation measured from the agglutinated fraction through the copper grid as a function of the amount of anti-BSA present in which the latex particles were added.

It should be understood, however, that this detailed description, while indicating preferred embodiments of the invention, is given by way of illustration only since various changes and modifications within the spirit and scope of the invention will become apparent to those skilled in the art.

We claim:

1. A solid-support immunoassay system for the simultaneous quantitative determination in a single test of a first one and a second one of moieties of antibodies or antigens in a sample, said system comprising:

a solid support coated with a first and a second moiety of distinct antibodies, antibody binders, or antigens; a solution containing a sample having a first one and a second one of moieties of antibodies or antigens that correspond and can selectively bind to one of said first or second moieties of distinct antibodies antibody binders, or antigens to from a first antibody-antigen complex and a second antibody-antigen complex on said solid support; distinct markers possessing characteristic infrared absorption for labelling first and second antibody-antigen complexes that result when said solid support is immersed in said solution to distinguish them from each other; and an interferometer assembly having a mid-infrared radiation source, means for converting the source radiation into an interferometric signal and for passing said interferometric signal through said antibody-antigen complexes, means for measuring the interferometric signal after its propagation through said antibody-antigen complexes, and means for processing said interferometric signal for determining the degree of attenuation of said interferometric signal at wavelengths corresponding to an absorption characteristic of said first one and said second one of said first and said second antigen-antibody labelled complexes, thereby simultaneously determining the amount of said first one and said second one of moieties of antigens or antibodies in said sample.

2. The solid support immunoassay system according to claim 1, wherein said solid support comprises a polymer membrane.

3. The solid support immunoassay system according to claim 1, wherein said solid support comprises a polymer film.

4. The solid support immunoassay system according to claim 1, wherein said solid support comprises a polymer film coated on an optically reflecting material.

5. The solid support immunoassay system according to claim 1, wherein said solid support comprises a polymer film coated on an optically transparent material.

6. The solid support immunoassay system according to claim 1, wherein said solid support comprises a latex particle.

7. A heterogeneous immunoassay method using the system according to claim 1 for the simultaneous determination of multiple analytes in a single test, comprising the steps of:

a) immersing the solid support in the solution to form a first labelled antibody-antigen complex and a second labelled antibody-antigen complex:

b) separating, subsequent to the formation of said first and second labelled antigen-antibody complexes, the free antigens or antibodies by decantation, aspiration or filtration; and c) measuring simultaneously the extent of attenuation of the interferometric signal subsequent to antigen-antibody complex formation in step a) at multiple wavelengths corresponding to the respective infrared absorption characteristic of said distinct markers.

8. A method according to claim 7, wherein said distinct markers are embedded within latex particles.

9. A solid-support immunoassay system for the simultaneous quantitative determination in a single test of a first one, a second one, and a third one of moieties of antibodies or antigens in a sample, said system comprising:

a solid support coated with a first, a second, and a third moiety of distinct antibodies, antibody binders, or antigens; a solution containing a sample having a first one, a second one, and a third one of moieties of antibodies or antigens that correspond and can selectively bind to one of said first, second, or third distinct moieties of antibodies, antibody binders, or antigens to form a first antibody-antigen complex a second antibody-antigen complex and a third antibody-antigen complex on said solid support; distinct markers possessing characteristic infrared absorption for labelling first, second, and third antibody-antigen complexes that result when said solid support is immersed in said solution to distinguish them from each other; and an interferometer assembly having a mid-infrared radiation source, means for converting the source radiation into an interferometric signal and for passing said interferometric signal through said antibody-antigen complexes, means for measuring the interferometric signal after its propagation through said antibody-antigen complexes, and means for processing said interferometric signal for determining the degree of attenuation of said interferometric signal at wavelengths corresponding to an absorption characteristic of said first, second, and third labelled antigen-antibody complexes, thereby simultaneously determining the amount of said first one, said second one, and said third one of moieties of antigens or antibodies in said sample.

10. A solid-support immunoassay system for the simultaneous quantitative determination in a single test of a plurality of moieties of antibodies or antigens in a sample, said system comprising:

a solid support coated with a plurality of moieties of distinct antibodies, antibody binders, or antigens; a solution containing a sample having a plurality of moieties of antibodies or antigens that correspond and can selectively bind to respective ones of said plurality of moieties of distinct antibodies, antibody binders, or antigens to form a plurality of antibody-antigen complex on said solid support; distinct markers possessing characteristic infrared absorption for labelling respective ones of the plurality of antibody-antigen complexes that result when said solid support is immersed in said solution to distinguish them from each other; and an interferometer assembly having a mid-infrared radiation source, means for converting the source radiation into an interferometric signal and for passing said interferometric signal through said antibody-antigen complexes, means for measuring the interferometric signal after its propagation through said antibody-antigen complexes, and means for processing said interferometric signal for determining the degree of attenuation of said interferometric signal at wavelengths corresponding to absorption characteristics of each of the plurality of labelled antigen-antibody complexes, thereby simultaneously determining the amount of each of said plurality of moieties of antigens or antibodies in said sample.

* * * * *